United States Patent [19]

Bellussi et al.

[11] Patent Number: 5,275,995
[45] Date of Patent: Jan. 4, 1994

[54] DEHYDROISOMERISATION CATALYST AND ITS USE IN THE PREPARATION OF ISOBUTENE FROM N-BUTANE

[75] Inventors: Giuseppe Bellussi, Piacenza; Aldo Giusti, Lucca; Laura Zanibelli, Milan, all of Italy

[73] Assignees: Eniricere S.p.A., Milan, Italy; Snamprogetti S.p.A.

[21] Appl. No.: 737,067

[22] Filed: Jul. 29, 1991

[30] Foreign Application Priority Data

Aug. 1, 1990 [IT] Italy .................. 21157 A/90

[51] Int. Cl.$^5$ ............................................ B01J 21/02
[52] U.S. Cl. .................. 502/207; 502/242; 502/258; 502/262; 502/355
[58] Field of Search ........... 502/200, 207, 242, 258, 502/262, 355

[56] References Cited

U.S. PATENT DOCUMENTS

| | | |
|---|---|---|
| 2,346,657 | 4/1944 | Bloch et al. . |
| 3,793,232 | 2/1974 | Duhaut et al. .......... 502/334 |
| 4,392,003 | 7/1983 | Kolombos et al. ......... 502/61 |
| 4,433,190 | 2/1984 | Sikkenga et al. . |
| 4,486,547 | 12/1984 | Imai et al. .......... 502/223 |
| 4,764,498 | 8/1988 | Wissner et al. ........... 502/251 |

FOREIGN PATENT DOCUMENTS

| | | |
|---|---|---|
| 0042252 | 12/1981 | European Pat. Off. . |
| 0080929 | 6/1983 | European Pat. Off. . |
| 787275 | 12/1957 | United Kingdom . |
| 811775 | 4/1959 | United Kingdom . |

*Primary Examiner*—Patrick P. Garvin
*Assistant Examiner*—Brant M. Peebles
*Attorney, Agent, or Firm*—George P. Hoarse, Jr.; Shea & Gould

[57] ABSTRACT

A catalyst is described for the preparation of isobutene by dehydroisomerisation of n-butane consisting of a solid, granular support of porous gamma-alumina on the surface of which catalytic quantities of platinum, silica and preferably also one or more promotors are deposited. In a perferred form of embodiment this catalyst is used with a second catalyst which may be formed of Boralite B or a solid granular support gamma-alumina on the surface of which catalytic quantities of silica are deposited.

The present invention relates also to the process of dehydroisomerisation of n-butane to isobutene in which the catalyst is used and the relative operating conditions.

8 Claims, No Drawings

DEHYDROISOMERISATION CATALYST AND ITS USE IN THE PREPARATION OF ISOBUTENE FROM N-BUTANE

DESCRIPTION

The present invention relates to a catalyst for the prepartion of isobutene by dehydroisomerisation of n-butane and the process that uses the said catalyst.

Isobutene is a valuable intermediate used in various chemical reactions, for example as a monomer in polymerization and copolymerization reactions, as an alkylation agent in the production of methyl tert-butyl ether (reaction with methanol) and in the production of isoprene (reaction with formaldehyde).

Isobutene is usally obtained as a by-product in refining processes such as thermal or catalytic cracking, or by means of a two-stage process in the first of which n-butane is isomerised catalytically to isobutane and the latter is dehydrogenated catalytically to isobutene.

Catalytic processes have recently been described which in a single reaction stage enable the conversion of n-alkanes into iso-olefines. In particular, in EP 42.252, isobutene is obtained by the dehydroisomerisation of n-butane in the presence of a catalyst formed by an element of Group IIIa of the Periodic Table, or the relative slat, and from a low-acidity support. In U.S. Pat. No. 4,433,190 the dehydroisomerisation reaction of an n-alkane into the corresponding iso-olefine is performed on a catalyst obtained by impregnating a porous crystalline boro-silicate called AMS-1B with a noble metal. These dehydroisomerisation processes fail to produce totally satisfactory results, particularly from the point of view of the limited yield of the desired product. There are also known state-of-the-art dehydrogenation catalysts comprising a support on which platinum or another noble metal has been deposited. These catalysts may contain promoters usually chosen among tin, indium, thallium or one of the alkaline-earth metals. These latter catalysts are generally used in dehydrogenation processes of long-chain paraffins, as described in U.S. Pat. No. 4,486,547 and in Italian Application for Patent IT 23.149/87, filed on 22nd Dec. 1987.

In BE 877205 a porous crystalline boro-silicate named Boralite B is described capable also of isomerising n-paraffin.

In U.S. Pat. No. 4,038,337 a process for the isomerisation of alkenes to iso-alkenes is described which uses a catalyst of alumina containing silica on its surface.

It is also known that n-butane can be dehydroisomerised to isobutene in a single stage using two-component catalytic systems, in which the first component is alumina onto which catalytic quantities of platinum and possibly one or more promotors are absorbed and the second component may be alumina on whose surface catalytic quantities of silica are deposited or may be Boralite B.

A new catalyst has now been found, comprising alumina which on its surface contains platinum, silica and preferably one or more promotors, which in suitable reaction conditions enables dehydroisomerisation of n-butane to isobutene in a single stage giving high yields of useful product.

Thus the prime object of the present invention is a catalyst (a) formed of a solid support of porous gamma-alumina on the surface of which are deposited catalytic quantities of platinum, silica and preferably, as promotors, tin and/or indium.

In a preferred form of embodiment this catalyst is used with a second catalyst (b) which may be formed of Boralite B or a granular solid support of porous gamma-alumina on the surface of which are deposited catalytic quantities of silica.

The support required for catalyst (a) is alumina in the gamma crystallographic form, which has a surface are of 100 to 400 m$^2$/g and a total volume of pores of 0.5 to 1.2 ml/g, in the form of granules, extrusions or pellets with a useful size for use in a fixed catalytic bed and generally varying from 0.4 to 5 mm.

Catalyst (a), required for the aims of the present invention, is formed of a gamma alumina with the abovedescribed characteristics, on which are deposited platinum in a quantity of 0.1 to 1% by weight and silica in a quantity of 0.5 to 5% by weight, preferably 1-2.5%.

Catalyst (a) preferably contains, as promotors, also tin in a quantity of 0.1 to 1% by weight and/or indium in a quantity of 0.05 to 1%. In this case the following weight ratios are suitably maintained: platinum/indium from 0.3:1 to 1.5:1 and platinum/tin from 0.5:1 to 2:1. All of the above percentages refer to the total weight of the catalyst. Catalyst (a) is prepared by means of a two-stage process consisting in:

1) thermally decomposing an alkyl ortho-silicate in the presence of gamma-alumina and treating the resulting product at high temperature, first in an inert atmosphere and then in an oxidizing atmosphere;

2) impregnating the silicified alumina obtained in the previous step with an acid aqueous solution, especially acidified with nitric acid, of a compound of platinum, and possibly tin and/or indium, then drying and calcining.

As regards the first step, relating to the preparation of silicified alumina, described and claimed in U.S. Pat. No. 4,013,590, suitable quantities of gamma-alumina and alkyl orthosilicate, preferably ethyl ortho-silicate, are placed in contact with each other at an operating temperature of 100° to 400° C., at a pressure of 10 to 30 kg/cm$^2$ and for a contact time of approx. 1 to 20 hours. This treatment is conducted in the absence of oxygen and humidity, presurizing with an inert gas, preferably nitrogen, at a temperature of 100° to 400° C., for a time varying of from 1 to 4 h, and then in an air flow at a temperature of 400° to 600° C. for a time of from 2 to 8 hours. As regards the second step in particular, hydrosoluble and high temperatures decomposable platinum, and possible tin and indium, compounds, such as chloroplatinic acid, stannic chloride, and indium nitrate, are used for impregnation.

Drying of the impregnated support is best performed at temperatures in the order of 100°-130° C. in an air flow and calcination is best carried out at 400°-600° C., in an air flow for a time in the order of 2-8 hours. The catalyst thus obtained is subject to a reduction treatment before use in the dehydroisomerisation reaction. This treatment, which can be carried out in the dehydroisomerisation reactor, is usually performed in a flow of hydrogen, at high temperatures (approx. 450°-650° C.) for a time in the order of 1-5 hours.

This catalyst is used in the dehydroisomerisation of n-butane to isobutene preferably with a second catalyst (b) formed of Boralite B or a granular solid support of porous gamma-alumina on the surface of which are deposited catalytic quantities of silica.

When catalyst (b) is silicified gamma-alumina, it is prepared by following the same procedure previously described in step 1) relating to the preparation of catalyst (a). Catalyst (b) thus obtained is subjected to a reduction treatment before its use in the dehydroisomerisation reaction. In the most preferred form, catalysts (a) and (b) are simultaneously subjected to such reduction treatment. Catalyst (b) may also be Boralite B. Boralite B is a zeolite described in BE 877205. In the anhydrous and calcined form it has the following molar composition with the components expressed as oxides:

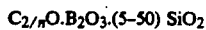
$C_{2/n}O.B_2O_3.(5-50) SiO_2$ where C=metallic cation of valence n, $H^+ m NH_4^+$, or a mixture of these.

Boralite B is prepared as described in BE 877205, by reaction in hydrothermal conditions with a derivative of silicon, a derivative of boron, an hydroxide of an alkaline metal and a salt of tetra-ethyl ammonium. More particularly, a derivative of silicon chosen for example from colloidal silica, silica gel or sodium silicate, a derivative of boron chosen for example from boric acid, alkaline borates or tri-alkyl borates, an hydroxide of alkaline metal and a salt of tetra-ethyl ammonium, preferably tetra-ethyl ammonium hydroxide, are heated in an autoclave at an autogenous pressure and at a temperature of between 90° C. and 160° C., until complete crystallisation. The crystalline product thus obtained is then filtered, dried and calcined. In particular, crystallisation preferably occurs in the presence of grains of Boralite B, in a quantity of between 1 and 60% by weight, which reduce the time required for synthesis.

These grains are obtained by placing a derivative of silicon, a derivative of boron, an hydroxide of an alkaline metal and a salt of tetra-alkyl ammonium to react in an autoclave, in the same ratios described in BE 877205, under hydrothermal conditions, for a period of at least one day. Boralite B is used in the present invention in the form of granules, extrusions or pellets of a suitable size for use in a fixed catalytic bed, generally variable between 0.4 and 5 mm.

A second object of the present invention is the process for preparing isobutene by dehydroisomerisation of n-butane making use of the above-mentioned catalyst (a), where such catalyst is used as it is or preferably with catalyst (b) described above.

The process according to the invention consists in supplying a gaseous mixture of n-butane and hydrogen, possibly diluted with an inert gas, to a fixed catalytic bed comprising catalyst (a), as it is or preferably with catalyst (b). In the gaseous supply flow a molar ratio between the hydrogen and n-butane of 1:1 to 5:1 should be maintained and preferably of from 1:1 to 3:1. If the gaseous supply flow is diluted, for example with nitrogen, the molar ratios between hydrogen and n-butane become comprised within the range of from 1:1 to 5:1 and that between nitrogen and n-butane within the range of from 1:1 to 5:1 and preferably of from 1:1 to 3:1.

The dehydroisomerisation reaction is conducted within a temperature range of 450° to 600° C., at a pressure of 200 mm Hg to 5 kg/cm$^2$ and at an hourly spatial speed of 0.5 to 5 hours$^{-1}$ (n-butane weight/catalyst weight.hour). Preferably the temperatures vary from 500° to 580° C., the pressures vary from 400 mm Hg to 2 kg/cm$^2$ and the spatial speed is between 2 and 4 hours$^{-1}$.

When catalyst (a) is used with catalyst (b) the said catalysts (a) and (b) are homogeneously distributed onto the catalytic bed, or are arranged in the form of two contiguous layers.

In this second case the layer of catalyst (a) will be arranged in the dehydroisomerisation reactor so as to come into contact firstly with the gaseous supply flow. The catalytic bed will also contain catalysts (a) and (b) in weight ratios between them of 20:80 to 80:20, preferably in the order of 70:30.

By operating in accordance with the process covered by the present invention high conversions of the n-butane supplied are obtained, with high yields and selectivity of the useful reaction product.

The experimental examples that follow are given as further illustration of the invention.

EXAMPLE 1

Preparing Catalyst (a)

The preparation of silicified alumina in this and the following examples is achieved in accordance with U.S. Pat. No. 4,013,590. For the preparation of catalyst (a) a commercial gamma-alumina is used, having a surface area of 196 m$^2$/g and a total volume of pores of 0.75 ml/g, in the form of granules of a size of 0.5–0.8 mm. 20 g of this gamma-alumina are placed in an autoclave together with 1.5 g of ethyl ortho-silicate. This is left to rest for 2 hours, then the autoclave is emptied to remove any excess ethyl ortho-silicate which has not reacted, washed with nitrogen to exclude the presence of oxygen and lastly brought to a pressure of 5 kg/cm$^2$ using nitrogen. The autoclave is heated to 200° C. and kept at that temperature for 4 hours. At the end of that period, after cooling, the pressure is discharged and the solid recovered and then subjected to further heat treatment of 2 hours at 200° C. in nitrogen and to calcination in air at 500° C. for 4 hours. Lastly after cooling, the solid consisting of gamma-alumina containing a layer of silica on its surface, is recovered in a quantity of 1.5% by weight. To 20 g of this solid 1.9 g of chloroplatinic acid is slowly added under agitation (to 4.21% by weight of platinum). After 12 hours of contact at ambient temperature the mass is heated to 120° C., in an air flow, for 1 hour, until the sample is dried. The dried solid thus obtained is calcined in a muffle at 500° C. for 4 hours in an air flow. Finally the autoclave is cooled and the catalyst (a) which is recovered, contains 0.4% by weight of platinum.

EXAMPLE 2

Preparing Catalyst (a) with Promotors

A commercial gamma-alumina is used having a surface area of 196 m$^2$/g and a total volume of pores of 0.75 ml/g, in the form of granules of a size of 0.5–0.8 mm. 20 g of this gamma-alumina are placed in an autoclave together with 1.5 g of ethyl ortho-silicate. This is left to rest for 2 hours, then the autoclave is emptied to remove any excess ethyl ortho-silicate which has not reacted, washed with nitrogen to exclude the presence of oxygen and lastly brought to a pressure of 5 kg/cm$^2$ using nitrogen. The autoclave is heated to 200° C. and kept at that temperature for 4 hours. At the end of that period after cooling, the pressure is discharged and the solid recovered and then subjected to further heat treatment of 2 hours at 200° C. in nitrogen and to calcination in air at 500° C. for 4 hours. Lastly, after cooling, the solid consisting of gamma-alumina containing a layer of silica on its surface, is recovered in a quantity of 1.5% by weight.

To 20 g of this gamma-alumina 30 ml of an aqueous solution obtained from 0.25 g of nitrate of indium pentahydrate, 0.2 g of stannic chloride, 0.47 g of chloroplatinic acid (to 16% by weight of platinum) and 1.3 g of nitric acid at 65% is slowly added under agitation. After one hour of contact at ambient temperature (about 25° C.), under continuous agitation, the mass is heated to about 120° C., in an air flow, for 1 hour, until the excess aqueous solvent is virtually completely evaporated. The dried solid thus obtained is calcined in a muffle at 500° C. for 4 hours in an air flow. Finally the autoclave is cooled and the catalyst (a) which is recovered, contains 0.37% by weight of platinum, 0.50% by weight of tin and 0.36% by weight of indium.

EXAMPLE 3

For the preparation of catalyst (b) a commercial gamma-alumina is used having a surface area of 196 $m^2/g$ and a total volume of pores of 0.75 ml/g, in the form of granules of a size of 0.5–0.8 mm. 20 g of this gamma-alumina are placed in an autoclave together with 1.5 g of ethyl ortho-silicate. This is left to rest for 2 hours, then the autoclave is emptied to remove any excess ethyl ortho-silicate which has not reacted, washed with nitrogen to exclude the presence of oxygen and lastly brought to a pressure of 5 $kg/cm^2$ using nitrogen. The autoclave is heated to 200° C. and kept at the temperature for 4 hours. At the end of that period after cooling, the pressure is discharged and the solid recovered and subjected to further heat treatment of 2 hours at 200° C. in nitrogen and to calcination in air at 500° C. for 4 hours. Lastly, after cooling, the solid consisting of gamma-alumina containing a layer of silica on its surface, is recovered in a quantity of 1.5% by weight.

EXAMPLE 4

Preparation of Boralite B

In 28.12 g of an aqueous solution of tetra-ethyl ammonium hydroxide at 40% by weight, 3.0 g of NaOH and 6.4 g of boric acid are dissolved. A clear solution is obtained which is diluted with 30 g of distilled water and added to 51 g of Ludox AS silica at 30% by weight of silica.

The suspension thus obtained, having a pH of 12.2, is left at ambient temperature under agitation for 4 hours and then placed to crystallise in an autoclave, in static conditions, at autogenous pressure, at 150° C., for 5 days.

The autoclave is then cooled and the milky suspension of grains of Boralite B is recovered. This suspension is added in quantities equal to 15% by weight to a mixture having the following composition, after the latter has been kept in agitation at ambient temperature for about 4 hours:

112.5 g of TEA-OH at 40% in water
12.0 g of NaOH
25.5 g of $H_3BO_3$
120.0 g of distilled water
204 g of Ludox AS silica at 30% by weight.

This mixture added to the suspension of grains is placed to crystallise in a steel autoclave under static conditions at an autogenous pressure, at a temperature of 150° C., for 3 days.

The autoclave is cooled, the Boralite B is recovered by filtration, it is washed with distilled water, dried at 120° C., calcined for 5 hours at 550° C. and then exchanged into acid form according to the known state-of-the-art methods. The Boralite B thus obtained, having crystals of a size of around 1 $\mu$m, is made into pellets with a granular size of 0.4 to 0.8 mm.

EXAMPLE 5

0.57 g of catalyst (a) prepared as described in Example 1 are placed in a quartz reactor with an internal diameter of 10 mm. The catalyst is subjected to in situ reduction, by supplying a flow of hydrogen for 2 hours, at a temperature of 550° C.

After this treatment the dehydroisomerisation test is performed by supplying the reactor with a gaseous mixture containing n-butane, hydrogen and nitrogen, with a hydrogen/n-butane molar ratio of 1:1 and a nitrogen/n-butane molar ratio of 2:1. In addition the test is conducted at a temperature of 553° C. at atmospheric pressure and with an hourly spatial speed of 2 $hours^{-1}$ (n-butane weight/catalyst weight.hour).

The results of the test are given in Table 1

EXAMPLE 6

0.34 g of catalyst (a) prepared as described in Example 2 are placed in a quartz reactor with an internal diameter of 10 mm. The catalyst is subjected to in situ reduction, by supplying a flow of hydrogen for 2 hours, at a temperature of 550° C.

After this treatment the dehydroisomerisation test is performed by supplying the reactor with a gaseous mixture containing n-butane, hydrogen and nitrogen, with a hydrogen/n-butane, molar ratio of 1:1 and a nitrogen/n-butane molar ratio of 2:1. In addition the test is conducted at a temperature of 563° C. at atmospheric pressure and with an hourly spatial speed of 2 $hours^{-1}$ (n-butane weight/catalyst weight.hour).

The results of the test are given in Table 1.

EXAMPLE 7

0.32 g of catalyst prepared as described in Example 2 are placed in a quartz reactor with an internal diameter of 10 mm. The catalyst is subjected to in situ reduction, by supplying a flow of hydrogen for 2 hours, at a temperature of 550° C.

After this treatment the dehydroisomerisation test is performed by supplying the reactor with a gaseous mixture containing n-butane, hydrogen and nitrogen, with a hydrogen/n-butane molar ratio of 1:1 and a nitrogen/n-butane molar ratio of 2:1. In addition the test is conducted at a temperature of 560° C. at atmospheric pressure and with an hourly spatial speed of 4 $hours^{-1}$ (n-butane weight/catalyst weight.hour).

The results of the test are given in Table 1.

EXAMPLE 8

0.33 g of catalyst (a) prepared as described in Example 2 and 0.31 g of catalyst (b) prepared as described in Example 3, are placed separately in a quartz reactor with an internal diameter of 10 mm.

The catalysts are subjected to in situ reduction, by supplying a flow of hydrogen for 2 hours, at a temperature of 550° C.

After this treatment the dehydroisomerisation test is performed by supplying the reactor with a gaseous mixture containing n-butane, hydrogen and nitrogen, with a hydrogen/n-butane molar ratio of 1:1 and a nitrogen/n-butane molar ratio of 2:1. In addition the test is conducted at a temperature of 563° C. at atmospheric pressure and with an hourly spatial speed, calculated for catalyst (a) only, of 2 hours$^{-1}$ (n-butane weight-/catalyst weight.hour).

The results of the test are given in Table 1.

EXAMPLE 9

0.50 g of catalyst (a) prepared as described in Example 2 and 0.25 g of catalyst (b) prepared as described in Example 4, are mixed until homogeneity and then placed in the form of a fixed bed in a quartz reactor with an internal diameter of 10 mm.

The catalysts are subjected to in situ reduction, by supplying a current of hydrogen for 2 hours, at a temperature of 550° C.

After this treatment the dehydroisomerisation test is performed by supplying the reactor with a gaseous mixture containing n-butane, hydrogen and nitrogen, with a hydrogen/n-butane molar ratio of 1:1 and a nitrogen/n-butane molar ratio of 2:1. In addition the test is conducted at a temperature of 564° C. at atmospheric pressure and with an hourly spatial speed, calculated for catalyst (a) only, of 2 hours$^{-1}$ (n-butane weight-/catalyst weight.hour).

The results of the test are given in Table 1.

EXAMPLE 10

0.86 g of catalyst (a) prepared as described in Example 2 and 0.33 g of catalyst (b) prepared as described in Example 4, are placed separately in a quartz reactor with an internal diameter of 10 mm and subjected to preliminary reduction in a flow of hydrogen at a temperature of 550° C., for 2 hours. After reduction the dehydroisomerisation test is performed by supplying the reactor with a gaseous mixture containing hydrogen, n-butane, and nitrogen, with a hydrogen/n-butane molar ratio of 1:1 and a nitrogen/n-butane molar ratio of 2:1. In addition the test is conducted at a temperature of 552° C. at atmospheric pressure and with an hourly spatial speed, assessed on catalyst (a), of 2 hours$^{-1}$ (n-butane weight/catalyst weight.hour).

The results of the test are given in Table 1.

EXAMPLE 11

0.86 g of catalyst (a) prepared as described in Example 2 and 0.33 g of catalyst (b) prepared as described in Example 4, are placed separately in a quartz reactor with an internal diameter of 10 mm and subjected to preliminary reduction in a flow of hydrogen at a temperature of 550° C., for 2 hours. After reduction the dehydroisomerisation test is performed by supplying the reactor with a gaseous mixture containing hydrogen, n-butane, and nitrogen, with a hydrogen/n-butane molar ratio of 1:1 and a nitrogen/n-butane molar ratio of 2:1. In addition the test is conducted at a temperature of 551° C. at atmospheric pressure and with an hourly spatial speed, assessed on catalyst (a), of 4 hours$^{-1}$ (n-butane weight/catalyst weight.hour).

The results of the test are given in Table 1.

EXAMPLE 12 (COMPARISON)

A crystalline borosilicate, called AMS-1B, is prepared as described in Example 1 of U.S. Pat. No. 4,269,813. More particularly, 10.5 g of boric acid and 67.2 g of sodium hydroxide are dissolved in 2,653 g of water under continuous agitation. To the solution thus obtained 394.8 g of tetra-n-propylammonium bromide and, after completely dissolving, 400 g of Ludox commercial silica are added. The solution is placed in an autoclave and left to crystallise at 165° C. for 7 days. The crystalline solid thus obtained is dried and calcined at 550° C. for 5 hours, exchanged into acid form and again dried and calcined. A sample of 4 g of this solid, in granules with a size of 0.5 to 0.8 mm, it impregnated with a solution of chloroplatinic acid at 16% by weight, so as to obtain a metallic platinum content of 0.55% by weight. Lastly, the solid is dried and calcined for 12 hours at 350° C. to obtain the catalyst. 0.34 g of the catalyst prepared as described above are placed in the quartz microreactor. Reduction is performed in a flow of hydrogen, at 525° C. for 2 hours. After this treatment the dehydroisomerisation test is performed. The supply to the reactor comprises n-butane, hydrogen and nitrogen, with a hydrogen/n-butane molar ratio of 1:1 and a nitrogen/n-butane molar ratio of 2:1. The reaction is performed at a temperature of 542° C., at atmospheric pressure and with an hourly spatial speed of 8 hours$^{-1}$. The results of the test are shown in Table 1.

EXAMPLE 13 (COMPARISON)

A sample of AMS-1B crystalline borosilicate prepared as described in Example 7, is mixed with 16 g of gamma-alumina. The mixture is granulated until the granular size is 0.5–0.8 mm and the granules are impregnated with a chloroplatinic acid solution at 4.1% by weight, according to Example 9 of U.S. Pat. No. 4,433,190. The impregnated solid is dried and calcined at 350° C. for 12 hours.

0.3 g of the catalyst thus obtained are placed in a quartz reactor. After the reduction treatment, performed in a flow of hydrogen at a temperature of 525° C. for two hours, the dehydroisomerisation test is performed. The supply comprises n-butane, hydrogen and nitrogen, with a hydrogen/n-butane molar ratio of 1:1 and a nitrogen/n-butane molar ratio of 2:1. The reaction is preformed at a temperature of 542° C., at atmospheric pressure and with an hourly spatial speed of 8 hours$^{-1}$.

The results of the test are given in Table 1.

In this Table, conversion means the percentage by weight of n-butane converted as compared to that supplied. Furthermore, the selectivity and yield relate to the converted reagent and supplied reagent respectively. Lastly, C1-C3 and C5+ indicate the paraffinic and olefinic products respectively containing from 1 to 3 carbon atoms and those with 5 or more carbon atoms.

TABLE 1

|  | Example No. | | | | | | | | |
| --- | --- | --- | --- | --- | --- | --- | --- | --- | --- |
|  | 5 | 6 | 7 | 8 | 9 | 10 | 11 | 12 | 13 |
| Conversion (%) | 45.1 | 46.3 | 56.3 | 56.8 | 57.8 | 58.4 | 58.5 | 8.1 | 33.7 |
| Selectivity (%) into: | | | | | | | | | |
| i-butene | 20.0 | 21.1 | 20.6 | 23.3 | 22.1 | 25.0 | 24.5 | 29.6 | 11.8 |
| n-butenes | 49.3 | 56.8 | 57.4 | 41.2 | 45.7 | 39.9 | 44.4 | 56.1 | 73.6 |
| Total C4s | 73.4 | 81.2 | 86.7 | 71.9 | 76.9 | 76.1 | 82.4 | 85.7 | 85.4 |
| Yield (%) in: | | | | | | | | | |

TABLE 1-continued

| | Example No. | | | | | | | | |
|---|---|---|---|---|---|---|---|---|---|
| | 5 | 6 | 7 | 8 | 9 | 10 | 11 | 12 | 13 |
| C1–C3 | 7.8 | 3.6 | 3.1 | 8.2 | 5.3 | 6.8 | 5.3 | 0.8 | 3.7 |
| C5+ | Traces | 1.2 | Traces | 1.6 | 1.8 | 2.8 | 1.9 | 0.3 | 1.2 |
| i-butene | 9.0 | 9.8 | 11.6 | 13.2 | 12.8 | 14.6 | 14.3 | 2.4 | 4.0 |
| aromatics | 2.7 | 1.9 | 1.7 | 5.5 | 4.7 | 4.4 | 2.9 | traces | 0.7 |

We claim:

1. A catalyst for the preparation of isobutene by dehydroisomerisation of n-butane, said catalyst formed of a solid granular support of porous gamma-alumina on the surface of which are deposited 0.1 to 1% by weight of platinum and 0.5 to 5% by weight of silica.

2. A catalyst in accordance with claim 1 containing in addition catalytic quantities of tin and/or indium.

3. A catalyst in accordance with claim 1, characterised in that the support is gamma-alumina with a surface area of 100 to 400 m$^2$/g and a total volume of pore of 0.5 to 1.5 ml/g, in the form of granules of a size of 0.4 to 5 mm.

4. A catalyst in accordance with claim 1 containing silica in a quantity of 1 to 2.5% by weight.

5. A catalyst in accordance with claim 2 containing tin in a quantity of 0.1 to 1% and indium in a quantity of 0.05 to 1% by weight, with the weight ratios of platinum/indium of 0.3:1 to 1.5:1 and platinum/tin of 0.5:1 to 2:1.

6. A process for the preparation of the catalyst as described in claim 1, said process consisting of:
 1. decomposing alkyl orthosilicate in the presence of gamma-alumina, at a temperature of between 100° and 400° C. at a pressure of 10 to 30 kg/cm$^2$ for a contact time of 1 to 20 hours, and treating the resulting product first in an inert atmosphere at a temperature of 100° to 400° C., for a time of 1 to 4 hours, and then in an oxidizing atmosphere at a temperature of 400° to 600° C. for a time of 2 to 8 hours;
 2. impregnating the product obtained in step 1) with an acid aqueous solution of a compound of platinum, and possibly tin/or indium, drying the said impregnated support at a temperature of 100° to 130° C. in an air flow and calcining at a temperature of 400° to 600° C. in an air flow for a time of 2 to 8 hours.

7. A catalytic system comprising a first catalyst, according to claim 1, and a second catalyst formed of porous gamma-alumina on the surface of which is deposited a catalytic quantity of silica.

8. A catalytic system comprising a first catalyst, according to claim 1, and a second catalyst formed of Boralite B having in its anhydrous and calcined form the following molar composition with the components expressed as oxides:

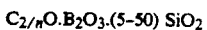

$$C_{2/n}O.B_2O_3.(5-50)\ SiO_2$$

where C is selected from a metallic cation of valence n, H$^+$, NH$_4^+$, or a mixture of these.

* * * * *